US00PP25518P2

(12) United States Plant Patent
Hanna et al.

(10) Patent No.: US PP25,518 P2
(45) Date of Patent: May 5, 2015

(54) GRASS 'TIFT 40'

(50) Latin Name: ***Pennisetum* hybrid**
Varietal Denomination: Tift 40

(71) Applicant: University of Georgia Research Foundation, Inc., Athens, GA (US)

(72) Inventors: Wayne W. Hanna, Chula, GA (US); S. Kristine Braman, Griffin, GA (US); Brian M. Schwartz, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 160 days.

(21) Appl. No.: 13/986,890

(22) Filed: Jun. 13, 2013

(51) Int. Cl.
*A01H 5/12* (2006.01)

(52) U.S. Cl.
USPC ..... Plt./384

(58) Field of Classification Search
USPC ..... Plt./384
See application file for complete search history.

*Primary Examiner* — Annette Para
(74) *Attorney, Agent, or Firm* — Klarquist Sparkman, LLP

(57) ABSTRACT

The new variety *Pennisetum* 'Tift 40' is provided. The new and distinct variety has high ornamental value, cold tolerance for short periods of time, and disease resistance. The asexually reproduced variety is reliably propagated vegetatively.

1 Drawing Sheet

Latin name of the genus and species of the plant claimed: 'Tift 40' is a tri-specific ornamental *Pennisetum* hybrid of the genus and species *Pennisetum purpureum*×[*Pennisetum glaucum*×(*Pennisetum purpureum*×*Pennisetum squamulatum*)].

Variety denomination: The new *Pennisetum* claimed is of the variety denominated 'Tift 40'.

BACKGROUND OF THE INVENTION

The present invention relates to a new and distinct cultivar of *Pennisetum* herein referred to as 'Tift 40'.

The new *Pennisetum* 'Tift 40' is a product of a planned breeding program conducted by the Inventors in Tifton, Ga. The objective of the *Pennisetum* breeding program is to create new plant cultivars with improved commercial qualities. This cultivar is commercially important for its superior ornamental value. These and other qualities are enumerated herein.

Pedigree and history: In 2003, red tetraploid (2n=4x=28) pearl millet (unpatented *Pennisetum glaucum*; designated '04-94') was crossed with SC 1125-2 [a Merkeron napiergrass (unpatented *Pennisetum purpureum;* 2n=4x=28) that had been crossed with PS 262 (unpatented *Pennisetum squamulatum;* 2n=8x=56)]. One vigorous plant, from the 04-94/SC 1125-2 cross, designated '04-26-1', was selected in 2004. In 2004, 'Princess' napiergrass (U.S. Plant Pat. No. 17,728; 2n=4x=28, female parent) was pollinated with '04-26-1' (unpatented; male parent). The new variety 'Tift 40' was the fortieth plant selected in 2005 from the 2004 cross. The new variety 'Tift 40' has been tested since 2006.

Asexual reproduction of the new *Pennisetum* 'Tift 40' by vegetative propagation (single stem propagules) in a controlled environment in Tifton, Blairsville, and Griffin, Ga. since 2006, has shown that the unique features of this new *Pennisetum* hybrid are stable and reproduced true to type in successive generations.

SUMMARY OF THE INVENTION

The following traits have been repeatedly observed and represent the characteristics of a new variety *Pennisetum*, 'Tift 40'. The new variety 'Tift 40' has not been observed under all possible environmental conditions. The phenotype may vary somewhat with variations in, for example, temperature, day-length, light intensity, soil types, and water and fertility levels without, however, any variance in genotype.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England.

The following traits have been repeatedly observed in Tifton, Blairsville, and Griffin, Ga., and are determined to be the unique characteristics of the new variety 'Tift 40':

1. 'Tift 40' reaches a height of about 1.7 meters, and a spread of about 1.8 meters.
2. 'Tift 40' exhibits a vigorous growth habit.
3. 'Tift 40' is pollen and seed sterile.

The new variety *Pennisetum* 'Tift 40' can be compared to its parents, 'Princess' and '04-26-01', and 'Princess Caroline', (U.S. Plant Pat. No. 21,464) a sister hybrid released in 2009 (Hanna, W. W., S. K. Braman, and B. M. Schwartz. 2010. 'Tift 17' and 'Tift 23' (unpatented) hybrid ornamental *Pennisetums*. Hortscience 45:135-138.

Plants of the new *Pennisetum* 'Tift 40' differ from its female parent 'Princess' in the following characteristics:

1. The new variety 'Tift 40' is taller than 'Princess'.
2. The leaf length and width of the new variety 'Tift 40' are longer and wider, respectively, compared to the leaf length and width of 'Princess'.

Plants of the new *Pennisetum* 'Tift 40' differ from its male parent '04-26-1' in the following characteristics:

1. The new variety 'Tift 40' is slightly different from '04-26-1' in adaxial leaf color. The new variety 'Tift 40' is about Greyed-purple RHS 187C, whereas '04-26-1' is about mottled Greyed-purple/green RHS 183B/138A.
2. The new variety 'Tift 40' has a different midrib color. The new variety 'Tift 40' is about Greyed-purple RHS 186A, while '04-26-1' is about Red-purple RHS 61C.

Plants of the new *Pennisetum* 'Tift 40' differ from its sister hybrid 'Princess Caroline' in the following characteristics:

1. The new variety 'Tift 40' is significantly taller than 'Princess Caroline'.
2. Culm-leaf angle is significantly larger for 'Tift 40' compared to 'Princess Caroline'.

The following observations, measurements, and values describe plants grown in Tifton, Blairsville, or Griffin, Ga. In Tables 1-5, the least significant difference (LSD) is set at P≤0.05 probability level. Growth days were included in ratings. Plants were spaced at 2 meter centers. All data are from plants established as single stem propagules in mid-May and rated in September through October, except the data from 2010 and 2011, in which the plants had been overwintered at Tifton, Ga.

The new variety 'Tift 40' was significantly taller than 'Princess Caroline' in five of seven tests in Tifton, Blairsville, and Griffin, Ga. (Table 1). The 2011 plants of Tift 40 were significantly shorter, probably due to the severe 2010/2011 winter. The canopy diameter for 'Tift 40' was equal to that of 'Princess Caroline' in four of seven tests and significantly wider in three of seven tests (Table 2). 'Tift 40' has an attractive reddish/purple color and had significantly better color than 'Princess Caroline' in four of seven tests and was equal in color in three tests (Table 3). The new variety 'Tift 40', similar to 'Princess Caroline', is not disease-susceptible to *Helminthosporium* leaf spot, whereas 'Princess' is susceptible to this disease (Table 4). Leaves of 'Tift 40' are significantly longer, wider, and have more leaf area than leaves of 'Princess Caroline' (Table 5). Culm-leaf angle was significantly less for 'Tift 40' compared to 'Princess Caroline' (Table 5).

TABLE 1

Plant heights (cm) of two ornamental *Pennisetum* grasses planted at three locations in Georgia.

| | Tifton | | | Blairsville | | | Griffin |
|---|---|---|---|---|---|---|---|
| | 2009 | 2010 | 2011 | 2009 | 2010 | 2011 | 2010 |
| Growth days | 153 d | 150 d | 183 d | 144 d | 145 d | 160 d | 124 d |
| 'Tift 40' | 142 | 111 | 75 | 172 | 133 | 160 | 132 |
| 'Princess Caroline' | 95 | 107 | 85 | 107 | 78 | 115 | 108 |
| LSD | 7 | NS | 10 | 24 | 15 | 25 | 24 |

In Table 1, plant heights were measured from ground level to top of plant canopy. All height measurements are in cm. At Tifton, Ga., 'Tift 40' and 'Princess Caroline' were planted on May 9, 2009, May 9, 2010, and May 12, 2011, with measurements taken on Oct. 12, 2009, Sep. 29, 2010, and Oct. 18, 2011. At Blairsville, Ga., 'Tift 40' and 'Princess Caroline' were planted on May 14, 2009, May 11, 2010, and May 1, 2011, with measurements made on Oct. 8, 2009, Oct. 6, 2010 and Oct. 10, 2011, respectively. At Griffin, Ga., 'Tift 40' and 'Princess Caroline' were planted on May 14, 2010, with measurements taken on Sep. 10, 2010.

TABLE 2

Canopy diameter (cm) of individual plant of two ornamental *Pennisetum* grasses planted at three locations in Georgia. Plants were spaced on two meter centers.

| | Tifton | | | Blairsville | | | Griffin |
|---|---|---|---|---|---|---|---|
| | 2009 | 2010 | 2011 | 2009 | 2010 | 2011 | 2010 |
| Growth days | 153 d | 150 d | 183 d | 144 d | 145 d | 160 d | 124 d |
| 'Tift 40' | 145 | 115 | 184 | 183 | 154 | 151 | 165 |
| 'Princess Caroline' | 135 | 129 | 131 | 152 | 146 | 162 | 155 |
| LSD | 7 | NS | 10 | 25 | NS | NS | NS |

Plant canopy measurements, as shown in Table 2, represent the average diameters measured at the estimated widest and narrowest portions of a single plant canopy. Measurements are in cm. At Tifton, Ga., 'Tift 40' and 'Princess Caroline' were planted on May 9, 2009, May 9, 2010, and May 12, 2011, with measurements taken on Oct. 12, 2009, Sep. 29, 2010, and Oct. 18, 2011. At Blairsville, Ga., 'Tift 40' and 'Princess Caroline' were planted on May 14, 2009, May 11, 2010 and May 1, 2011, with measurements made on Oct. 8, 2009, Oct. 6, 2010 and Oct. 10, 2011. At Griffin, Ga., 'Tift 40' and 'Princess Caroline' were planted on May 14, 2010, with measurements taken on Sep. 10, 2010.

TABLE 3

Color ratings on individual plants of two ornamental *Pennisetum* grasses planted at three locations in Georgia. Plants were spaced on two meter centers.

| | Tifton | | | Blairsville | | | Griffin |
|---|---|---|---|---|---|---|---|
| | 2009 | 2010 | 2011 | 2009 | 2010 | 2011 | 2010 |
| Growth days | 153 d | 150 d | 183 d | 144 d | 145 d | 160 d | 124 d |
| 'Tift 40' | 8.0 | 7.0 | 8.3 | 8.0 | 9.0 | 8.3 | 8.0 |
| 'Princess Caroline' | 8.0 | 7.1 | 7.6 | 7.3 | 7.6 | 7.6 | 8.0 |
| LSD | NS | NS | 0.6 | 0.7 | 0.8 | 0.6 | NS |

Color ratings are measured on a scale of 1 to 9, where 1 represents green and 9 represents dark purple/red. At Tifton, Ga., 'Tift 40' and 'Princess Caroline' were planted May 9, 2009, May 9, 2010, and May 12, 2011, with measurements taken on Oct. 12, 2009, Sep. 29, 2010, and Oct. 18, 2011. At Blairsville, Ga., 'Tift 40' and 'Princess Caroline' were planted on May 14, 2009, May 11, 2010 and May 1, 2011, with measurements taken on Oct. 8, 2009, Oct. 6, 2010 and Oct. 10, 2011. At Griffin, Ga., 'Tift 40' and 'Princess Caroline' were planted on May 14, 2010, with measurements taken September 10, 2010.

TABLE 4

*Helminthosporium* leaf spot ratings on two ornamental *Pennisetum* grasses planted at two locations in Georgia.

| | Tifton | | | Blairsville | |
|---|---|---|---|---|---|
| | 2009 | 2010 | 2011 | 2010 | 2011 |
| Growth days | 153 d | 150 d | 183 d | 145 d | 160 d |
| 'Tift 40' | 1.0 | 1.0 | 1.0 | 1.0 | 1.0 |
| 'Princess Caroline' | 1.0 | 1.0 | 1.0 | 1.0 | 1.0 |
| 'Princess' | 5.2 | 6.6 | 8.0 | 5.0 | 7.6 |
| LSD | 0.4 | 0.1 | 0.0 | 1.2 | 0.2 |

Disease ratings in Table 9 are defined as follows: 1=No disease, 2=1-20%, 3=21-30%, 4=31-40%, 5=41-50%, 6=51-60%, 7=61-70%, 8=71-80%, 9=>80% leaves infected. Symptoms occur in the field during late August and September. At Tifton, Ga., 'Tift 40' and 'Princess Caroline' were planted on May 9, 2009, May 9, 2010, and May 12, 2011, with measurements taken on Oct. 12, 2009, Sep. 29, 2010, and Oct. 18, 2011. At Blairsville, Ga., 'Tift 40' and 'Princess Caroline' were planted on May 11, 2010 and May 1, 2011, with measurements taken on Oct. 6, 2010 and Oct. 10, 2011.

TABLE 5

Leaf characteristics of individual plants of two ornamental *Pennisetum* grasses planted at Tifton, Georgia in 2009. Plants were spaced on two meter centers.

| Entry | Leaf Length (cm) | Leaf Width(mm) | Leaf Area ($cm^2$) | Leaf Angle Culm:Leaf (degrees) |
|---|---|---|---|---|
| 'Tift 40' | 83 | 45 | 258 | 27 |
| 'Princess Caroline' | 72 | 37 | 179 | 18 |
| LSD | 6 | 4 | 33 | 2 |

The leaf length was measured in cm from the leaf collar to the leaf tip of the latest fully extended leaf. The leaf width was measured in mm in the center of the latest fully extended leaf. The leaf area was measured in $cm^2$ using a LiCor area meter using the mean of three leaves per replication. The measured leaf angle was the angle observed between the adaxial leaf angle surface and the culm at the leaf collar on the last fully extended leaf and was measured in degrees. At Tifton, Ga., 'Tift 40' was planted on May 9, 2009, with measurements taken on Sep. 12, 2009.

TABLE 6

Summary of morphological characteristics of two *Pennisetum* grasses.

| Trait | 'Princess Caroline' | 'Tift 40' |
|---|---|---|
| Mature plant height | 95-115 cm | 111-172 cm |
| Diameter of plant canopy | 129-162 cm | 115-183 cm |
| Leaf width | 37 mm | 45 mm |
| Leaf length | 72 cm | 83 cm |
| Leaf Area-$cm^2$ | 179 | 258 |
| Leaf Angle (Stem:Leaf) | 18 degrees | 27 degrees |
| Adaxial leaf surface trichomes | None | None |
| Abaxial leaf surface trichomes | None | None |
| Leaf blade margin trichome length | <0.1 mm | 0.5 mm |
| Leaf collar trichome length | 3 mm | Dense, 3 mm |
| Leaf blade edge at collar Trichome | 6 mm long for 6 cm from collar | 4 mm long for 12 cm from collar |
| Sheath trichomes | 2 mm long for 2 cm from collar | None |
| Adaxial leaf color | Greyed-purple 187D | Greyed-purple 187C |
| Abaxial leaf color | Greyed-purple 187D | Greyed-purple 187A |
| Midrib color | Greyed-purple 187D | Greyed-purple 186A |
| Inflorescences on Dec. 21, 2009 | None | None |
| Number of culms on mature plants | 27-65 | 25-58 |
| *Helminthosporium* leaf spot on mature plants | None | None |

In summary, 'Tift 40' is similar to 'Princess Caroline' in disease resistance and is either equal in color or has significantly better color. 'Tift 40' tends to be taller, has longer, wider leaves with more leaf area per leaf and a smaller stem: leaf angle than 'Princess Caroline'.

BRIEF DESCRIPTION OF THE FIGURES

The accompanying colored photographs illustrate the overall appearance and distinct characteristics of the new variety of *Pennisetum* 'Tift 40'. The colors in the photographs are as close as possible with the photographic and printing technology utilized.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart.

FIG. 1 is a photograph of the new variety *Pennisetum* 'Tift 40'.

BOTANICAL DESCRIPTION

The new variety 'Tift 40' is a perennial at Tifton, Ga. (USDA Zone 8a). The new variety 'Tift 40' survived −6° C. for one night and 21 nights below 0° C. in the field during the 2009/2010 winter at Tifton. It did not survive the winter temperatures (−7° C. for one night and 24 nights below 0° C. in the field during 2010/2011) in Tifton. It has not survived the winter temperatures at Griffin, Ga. (USDA Zone 7b) or in the mountains of Blairsville, Ga. (USDA Zone 6b). Because of its vigor, 'Tift 40' can effectively be used as an annual where it will not survive freezing temperatures in the winter.

All data are from plants established as single stem propagules in mid-May, and rated in September through October, except the 2010 and 2011 data are from plants that over-wintered at Tifton. Plants were spaced at 2 meter centers.

Plant:

*Mature plant height*.—Approximately 111-172 cm.

*Diameter of plant canopy*.—Approximately 115-183 cm.

Leaf:

*Leaf width*.—Approximately 45 mm.

*Leaf length*.—Approximately 83 cm.

*Adaxial leaf surface trichomes*.—None.

*Abaxial leaf surface trichomes*.—None.

*Leaf blade margin trichome length*.—0.5 mm.

*Leaf collar trichome length*.—Dense, 3 mm.

*Leaf blade edge at collar trichome*.—4 mm long for 12 cm from collar.

*Sheath trichomes*.—None.

*Adaxial leaf color*.—About Greyed-purple RHS 187C.

*Abaxial leaf color*.—About Greyed-purple RHS 187A.

*Midrib color*.—About Greyed-purple RHS 186A.

*Helminthosporium leaf spot on mature plants*.—None.

*Inflorescence*.—None.

Culm:

*Number of culms on mature plants*.—25-58.

What is claimed is:

1. A new and distinct variety of the *Pennisetum* plant named 'Tift 40', substantially as illustrated and described herein.

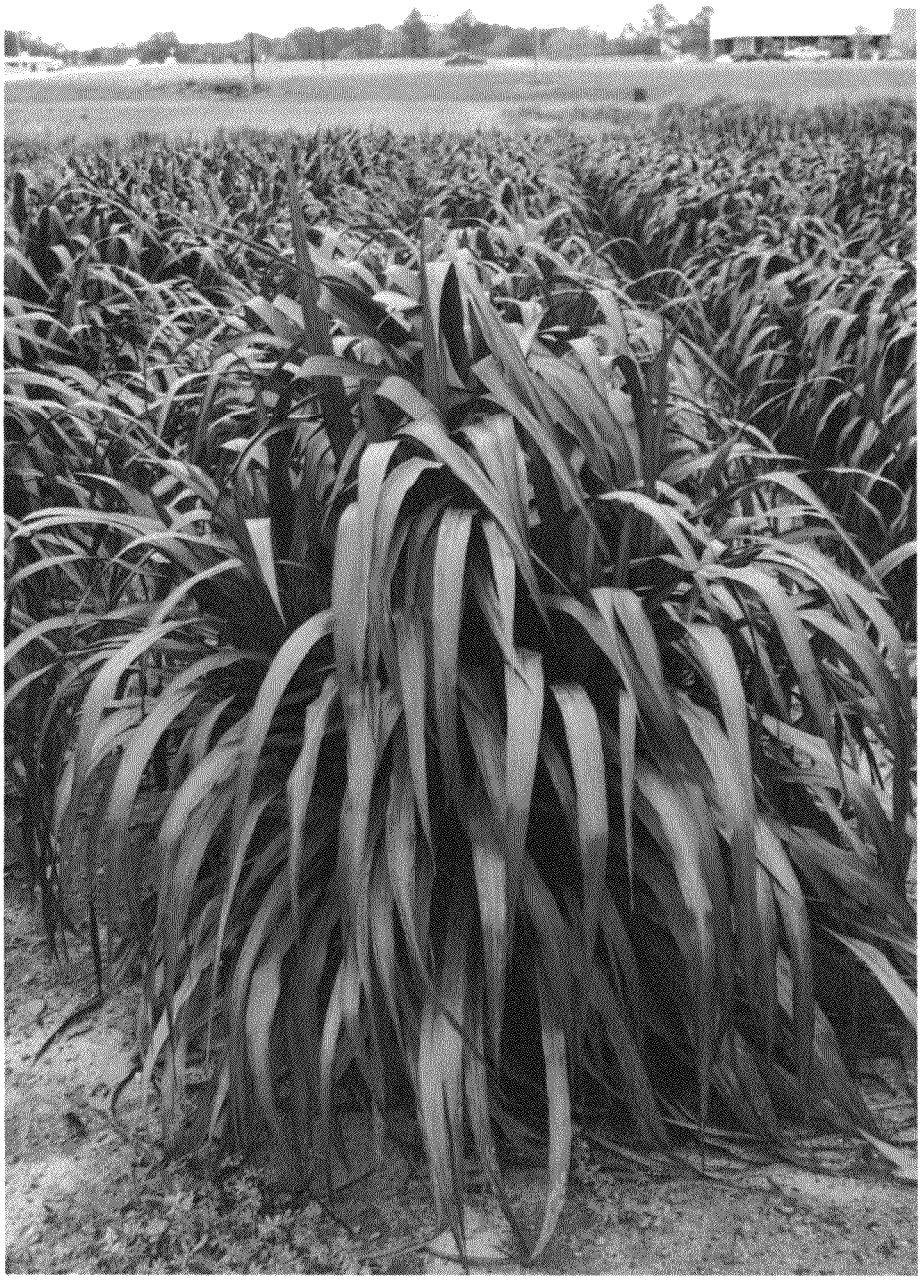

* * * * *